(12) United States Patent
Cornblatt et al.

(10) Patent No.: US 11,224,639 B2
(45) Date of Patent: *Jan. 18, 2022

(54) COMPOSITIONS COMPRISING SULFORAPHANE OR A SULFORAPHANE PRECURSOR AND A MILK THISTLE EXTRACT OR POWDER

(71) Applicant: Nutramax Laboratories, Inc., Lancaster, SC (US)

(72) Inventors: Brian Cornblatt, Westminster, MD (US); Grace Cornblatt, Westminster, MD (US); Anton Bzhelyansky, Baltimore, MD (US); Robert Henderson, Street, MD (US)

(73) Assignee: Nutramax Laboratories, Inc., Lancaster, SC (US)

(*) Notice: Subject to any disclaimer, the term of this patent is extended or adjusted under 35 U.S.C. 154(b) by 0 days.

This patent is subject to a terminal disclaimer.

(21) Appl. No.: 16/865,529

(22) Filed: May 4, 2020

(65) Prior Publication Data
US 2020/0261553 A1 Aug. 20, 2020

Related U.S. Application Data

(63) Continuation of application No. 14/412,176, filed as application No. PCT/US2013/049261 on Jul. 3, 2013, now Pat. No. 10,688,158.

(60) Provisional application No. 61/794,417, filed on Mar. 15, 2013, provisional application No. 61/668,396, filed on Jul. 5, 2012, provisional application No. 61/668,328, filed on Jul. 5, 2012, provisional application No. 61/668,374, filed on Jul. 5, 2012, provisional application No. 61/668,364, filed on Jul. 5, 2012, provisional application No. 61/668,386, filed on Jul. 5, 2012, provisional application No. 61/668,342, filed on Jul. 5, 2012.

(51) Int. Cl.
| | |
|---|---|
| A61K 38/47 | (2006.01) |
| A23L 33/105 | (2016.01) |
| A61K 36/31 | (2006.01) |
| A61K 31/375 | (2006.01) |
| A61K 31/7028 | (2006.01) |
| A61K 33/06 | (2006.01) |
| A61K 9/14 | (2006.01) |
| A61P 3/06 | (2006.01) |
| A61K 31/26 | (2006.01) |
| A61K 36/07 | (2006.01) |
| A61K 45/06 | (2006.01) |
| A61K 9/00 | (2006.01) |
| A61K 9/28 | (2006.01) |
| A61K 31/194 | (2006.01) |
| A61K 47/42 | (2017.01) |
| A61K 31/19 | (2006.01) |
| A61K 36/28 | (2006.01) |
| A61K 31/716 | (2006.01) |
| A61K 36/06 | (2006.01) |
| A61K 31/357 | (2006.01) |

(52) U.S. Cl.
CPC ............ *A61K 38/47* (2013.01); *A23L 33/105* (2016.08); *A61K 9/0053* (2013.01); *A61K 9/14* (2013.01); *A61K 9/28* (2013.01); *A61K 31/19* (2013.01); *A61K 31/194* (2013.01); *A61K 31/26* (2013.01); *A61K 31/357* (2013.01); *A61K 31/375* (2013.01); *A61K 31/7028* (2013.01); *A61K 31/716* (2013.01); *A61K 33/06* (2013.01); *A61K 36/06* (2013.01); *A61K 36/07* (2013.01); *A61K 36/28* (2013.01); *A61K 36/31* (2013.01); *A61K 45/06* (2013.01); *A61K 47/42* (2013.01); *A61P 3/06* (2018.01); *C12Y 302/01147* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 7,544,356 B2 | 6/2009 | Lim et al. | |
| 9,421,183 B2 * | 8/2016 | Cornblatt | ................. A61K 9/14 |
| 10,583,178 B2 * | 3/2020 | Cornblatt | ............. A61K 9/0053 |
| 10,688,158 B2 * | 6/2020 | Cornblatt | ............... A61K 36/06 |
| 2006/0233774 A1 | 10/2006 | Lim et al. | |

(Continued)

FOREIGN PATENT DOCUMENTS

| | | |
|---|---|---|
| DE | 102005033616 A1 | 1/2007 |
| EP | 2087902 A1 | 8/2009 |

(Continued)

OTHER PUBLICATIONS

Ribavirin (Oral Route), 2020, Mayo Clinic https://www.mayoclinic.org/drugs-supplements/ribavirin-oral-route/description/drg-20071471 (Year: 2020).*

(Continued)

*Primary Examiner* — Abigail Vanhorn
*Assistant Examiner* — Ali S Saeed
(74) *Attorney, Agent, or Firm* — Dickinson Wright PLLC; Andrew D. Dorisio

(57) ABSTRACT

The invention relates to the combination of a sulforaphane precursor, an enzyme capable of converting the sulforaphane precursor to sulforaphane, an enzyme potentiator, and a milk thistle extract or powder. The invention also relates to the combination of a sulforaphane or a derivative thereof and a milk thistle extract or powder. The invention also relates to the combination of a broccoli extract or powder and a milk thistle extract or powder. The invention provides compositions and methods relating to these combinations.

20 Claims, 6 Drawing Sheets

(56) References Cited

U.S. PATENT DOCUMENTS

| | | | |
|---|---|---|---|
| 2007/0021376 A1 | 1/2007 | Giampapa | |
| 2008/0311192 A1* | 12/2008 | West | A61P 39/00 |
| | | | 424/463 |
| 2010/0015109 A1 | 1/2010 | Bias | |
| 2013/0045273 A1* | 2/2013 | Cuomo | A23L 33/10 |
| | | | 424/451 |
| 2020/0101143 A1* | 4/2020 | Cornblatt | A61K 36/31 |
| 2021/0008176 A1* | 1/2021 | Cornblatt | A61K 31/375 |

FOREIGN PATENT DOCUMENTS

| | | | |
|---|---|---|---|
| JP | 2006298917 A | 11/2006 | |
| WO | 0007607 A1 | 2/2000 | |
| WO | WO-0007607 A1 * | 2/2000 | A61K 36/45 |
| WO | 2007013987 A2 | 2/2007 | |
| WO | 2012122295 A2 | 9/2012 | |

OTHER PUBLICATIONS

Sarah J. Schrieber, Differences in the Disposition of Silymarin between patients with nonalcoholic fatty liver disease and chronic hepatitis C, 2011, DMD, 39:2182-2190 (Year: 2011).*

Okano, et al., Chemoprevention against hepatocellular carcinoma, Clinical Journal of Gastroenterology, vol. 4, No. 3, pp. 185-197, Jun. 1, 2011.

English Machine Translation of JP 2006298917.

Shen, et al., Endogenous and exogenous enzymolysis of vegetable-sourced glucosinolate and influencing factors, Food Chemistry 119 (2010) 987-994.

Hajaghamohammadi, et al., The Efficacy of Silymarin in Decreasing Transaminase Activities in Non-Alcoholic Fatty Liver Disease: A Randomized Controlled Clinical Trial, Hepatitis Monthly, 2008, vol. 3, pp. 191-195.

English Machine Translation of DE102005033616.

Jacobs, B., et al., Milk Thistle for the Treatment of Liver Disease: A Systematic Review and Meta-Analysis; Am. J. of Medicine, Oct. 15, 2002 vol. 113, pp. 506-515.

Li, Y., et al., Sulforaphane, a Dietary Component of Broccoli/Broccoli Sprouts, Inhibits Breast Cancer Stem Cells; Clin. Cancer Res. May 1, 2010; 16(9); 19 pp.

Extended European Search Report from the European Patent Office; dated Sep. 20, 2018 for related application European Divisional Patent Application No. 18182247.9.

IP Australia Examination Report No. 1 dated Jun. 19, 2019 in related Australian Patent Application No. 2018204283.

* cited by examiner

COMPOSITIONS COMPRISING SULFORAPHANE OR A SULFORAPHANE PRECURSOR AND A MILK THISTLE EXTRACT OR POWDER

This application is a continuation of U.S. application Ser. No. 14/412,176, filed on Dec. 30, 2014, which is a national stage application of international patent application no. PCT/US13/49261 filed on Jul. 3, 2013, which claims priority to the following applications: U.S. Provisional Patent Application No. 61/668,328, filed on Jul. 5, 2012; U.S. Provisional Patent Application No. 61/668,342, filed on Jul. 5, 2012; U.S. Provisional Patent Application No. 61/668,386, filed on Jul. 5, 2012; U.S. Provisional Patent Application No. 61/668,396, filed on Jul. 5, 2012; U.S. Provisional Patent Application No. 61/668,364, filed on Jul. 5, 2012; U.S. Provisional Patent Application No. 61/668,374, filed on Jul. 5, 2012; and U.S. Provisional Patent Application No. 61/794,417, filed on Mar. 15, 2013, the disclosures of all of which are incorporated herein by reference in their entirety.

TECHNICAL FIELD

The present invention relates to the combination of a sulforaphane precursor, an enzyme capable of converting the sulforaphane precursor to sulforaphane, an enzyme potentiator, and a milk thistle extract or powder. The present invention also relates to the combination of a sulforaphane or a derivative thereof and a milk thistle extract or powder. The present invention also relates to the combination of a broccoli extract or powder and a milk thistle extract or powder. The present invention provides compositions and methods relating to these combinations.

BACKGROUND

The use of natural products is becoming increasingly popular with humans and companion animals. Some of these natural products are being incorporated into dietary supplements and medical foods. There is a need in the art for supplements which are useful as chemoprotective and/or antioxidant agents. In addition, there is a need in the art for pharmaceutical compositions and dietary supplements which are useful for conditions and disorders associated with glutathione. Chemoprotection through the use of natural products is evolving as a safe, effective, inexpensive, easily accessible, and practical means to prevent or reduce the occurrence of many conditions affecting humans and domesticated animals. It is known that carcinogens which can damage cells at the molecular level are often ingested and inhaled as non-toxic precursors. These non-toxic precursors may then convert into carcinogenic substances in the body. Chemoprotective agents, such as natural substances which can activate detoxifying enzymes or their co-factors, can counteract and allow for the elimination of carcinogens. These same natural substances can potentiate other naturally existing defenses such as the immune system.

Some natural products have antioxidant activity. Oxidative stress plays a major role in aging, the progression of neurodegenerative diseases as well as physiological trauma, such as ischemia. Antioxidant agents can reduce or inhibit the oxidation of vital biomolecules and may play a role in treating, preventing, or reducing the occurrence of conditions affected by oxidative stress.

Some natural products are useful for enhancing liver health. Non-alcoholic fatty liver disease (NAFLD) is the most common liver disease in the U.S., affecting about 30% of the population. NAFLD is also known as hepatic lipidosis. In 10% of those with NAFLD, the disease will progress to non-alcoholic steatohepatitis (NASH), of which 25% will develop cirrhosis. Potentially 10-25% of those patients with cirrhosis will develop hepatocellular carcinoma. At the current rate and without effective treatment modalities, by 2030 hepatocellular carcinoma is projected to be the number one diagnosed cancer in the United States. NAFLD occurs when fat is deposited in the liver (steatosis), but not as a result of excessive alcohol use. NAFLD is associated with chronic inflammation, insulin resistance, diabetes and obesity. NAFLD presents few or no symptoms and is most commonly detected following abnormal results obtained during routine blood tests (i.e., elevated serum ALT and AST levels) and confirmed by an ultrasound or a biopsy. There are currently no surgical or pharmacological treatments for NAFLD. Recommendations to control NAFLD include lifestyle modifications such as eating a healthy diet, exercise, weight loss, lowering cholesterol and controlling diabetes.

NAFLD is often associated with a decrease in glutathione levels. Glutathione is a tripeptide with a gamma peptide linkage between the amine group of cysteine and the carboxyl group of the glutamate side chain. Glutathione plays an important role in the body, as it can serve as an antioxidant, detoxifier, and immunity enhancer. Glutathione can conjugate to metabolites and toxins, such as procarcinogens, for excretion from the body. Glutathione levels can be reduced in patients for a number of reasons, including poor diet, pollution, exposure to toxins and/or certain medications, stress, trauma, aging, infections, and radiation. Low levels of glutathione can cause a patient to be susceptible to oxidative stress, illness, and cancer. For example, reduced levels of glutathione are associated with conditions relating to the liver, prostate, brain, lung, kidneys, colon, breast, esophagus, pancreas, ovaries, etc. Examples of disorders associated with reduced levels of glutathione and glutathione deficiency include, but are not limited to: NAFLD, cancer (lung, prostate, colon, breast, brain, liver, ovarian, esophageal, pancreatic, nasopharyngeal, osteosarcoma), leukemia, cystic fibrosis, HIV, glutathione synthetase deficiency, Alzheimer's disease, Parkinson's disease, Huntington's disease, amyotrophic lateral sclerosis, Friedreich's ataxia, multiple sclerosis, fibromyalgia, chronic fatigue, autism, and diabetes.

An example of a natural product thought to have chemoprotective and antioxidant properties is sulforaphane. Sulforaphane is an organosulfur compound which is also known as 1-isothiocyanato-4-methylsulfinylbutane. The sulforaphane precursor, glucoraphanin, can be obtained from vegetables of the Brassicaceae family, such as broccoli, brussels sprout, and cabbage. However, copious amounts of vegetables must be consumed in order to obtain levels adequate for chemoprevention. Glucoraphanin is converted into sulforaphane by a thioglucosidase enzyme called myrosinase, which occurs in a variety of exogenous sources such as Brassicaceae vegetables and endogenously in the gut microflora. However, upon ingestion of glucoraphanin, not all animals are capable of achieving its conversion to sulforaphane, most likely due to variations in microflora populations and overall health. In addition, in acidic environments such as the stomach, glucoraphanin can be converted to inert metabolites. The active metabolite, sulforaphane is able to induce nuclear factor erythroid-2-related factor (Nrf2) which, in turn, upregulates the production of Phase II detoxification enzymes and cytoprotective enzymes such as glutathione S-transferases, NAD(P)H:quinine oxidoreductase (NQO1), and heme-oxygenase-1 (HO-1). Sulforaphane has been thought to induce the production of these enzymes without significantly changing the synthesis of P-450 cytochrome enzymes. The upregulation of Phase II enzymes is thought to play a role in a variety of biological activities, including the protection of the brain from cytotoxicity, the protection of the liver from the toxic effects of fat accumulation, and the detoxification of a variety of other tissues.

Sulforaphane and its precursor glucoraphanin have been studied extensively. Shapiro et al. (*Nutrition and Cancer*, (2006), Vol. 55(1), pp. 53-62) discusses a clinical Phase I study determining the safety, tolerability, and metabolism of broccoli sprout glucosinolates and isothiocyanates. Shapiro et al. discusses a placebo-controlled, double-blind, randomized clinical study of sprout extracts containing either glucosinolates such as glucoraphanin or isothiocyanates such as sulforaphane in healthy human subjects. The study found that administration of these substances did not result in systematic, clinically significant, adverse effects.

Milk thistle (*Silybum marianum*) is a plant of the Asteraceae family. Milk thistle contains silymarin, which is composed of a number of constituents, including, but not limited to flavonolignans such as silibinin (also known as silybin or silibin), isosilibinin, silichristin, silydianin, kvercetin, dehydrosilybin, deoxysilycistin, deoxysilydianin, silandrin, silybinome, silyhermin and neosilyhermin. Silymarin constituents can have a number of biological effects, including inhibition of free radical formation, binding of free radical species, prevention of membrane lipid peroxidation, increase in levels of glutathione, and chelation of iron. Silibinin is the major active constituent of silymarin, and it thought that have hepatoprotective properties. Silymarin is discussed in U.S. Pat. No. 7,563,779, which is incorporated herein in its entirety.

Zhang et al. (*Proc. Natl. Acad. Sci.*, (1994), Vol. 91, pp. 3147-3150) discusses a study in Sprague-Dawley rats to determine the anticarcinogenic activities of sulforaphane and structurally related synthetic norbornyl isiothiocyanates. The study determined that administration of sulforaphane was effective in blocking the formation of mammary tumors.

Cornblatt et al. (*Carcinogenesis*, (2007), Vol. 38(7): pp. 1485-1490) discusses a study in Sprague-Dawley rats to determine the effect of sulforaphane in chemoprevention in the breast. The study determined that oral administration of either sulforaphane or glucoraphanin resulted in a 3-fold increase in NAD(P)H:quinine oxidoreductase (NQO1) enzymatic activity and a 4-fold elevated immunostaining of the heme oxygenase-1 (HO-1) enzyme in the mammary epithelium.

Munday et al. (*Cancer Res*, (2008), Vol. 68(5): pp. 1593-1600) discusses a study regarding the effects of a freeze-dried aqueous extract of broccoli sprouts on bladder cancer development in rats. The study found that administration of the broccoli sprout extract resulted in a significant induction of glutathione S-transferase and NAD(P)H:quinine oxidoreductase 1 in the bladder, which are enzymes exerting protective activity against oxidants and carcinogens.

Aghazadeh S et al. (*Exp Toxicol Pathol*. (2011) September; 63(6):569-74) discuss the anti-apoptotic and anti-inflammatory effects of *Silybum marianum* in treatment of experimental steatohepatitis. The study found that administration of an extract of *Silybum maranium* to rats fed a methionine and choline deficient (MCD) diet to induce non-alcoholic steatohepatitis had improved AST and ALT activity along with an increase in the glutathione content compared to control rats being fed the MCD diet alone.

European Patent Application No. 2 213 280 discloses formulations comprising glucosinolates such as glucoraphanin, and myrosinase, wherein the formulation is encapsulated or coated.

All references cited herein are incorporated by reference in their entirety.

SUMMARY

The present invention provides a composition comprising: (i) a sulforaphane precursor, preferably glucoraphanin; (ii) an enzyme capable of converting the sulforaphane precursor to sulforaphane, preferably a glucosidase enzyme, more preferably a thioglucosidase enzyme, and most preferably myrosinase; (iii) an enzyme potentiator, preferably ascorbic acid; and (iv) a milk thistle extract or powder. The present invention also provides a method of treating, preventing, reducing the occurrence of, decreasing the symptoms associated with, and/or reducing secondary recurrences of, a disease or condition associated with the liver, prostate, brain, lung, kidneys, colon, breast, esophagus, pancreas, or ovaries in a subject, comprising administering to the subject: (i) a sulforaphane precursor, (ii) an enzyme capable of converting the sulforaphane precursor to sulforaphane, (iii) an enzyme potentiator, and (iv) a milk thistle extract or powder. The present invention also provides a method of increasing glutathione levels in a subject in need thereof in a subject, comprising administering to the subject: (i) a sulforaphane precursor, (ii) an enzyme capable of converting the sulforaphane precursor to sulforaphane, (iii) an enzyme potentiator, and (iv) a milk thistle extract or powder. The present invention also provides a method of treating, preventing, reducing the occurrence of, decreasing the symptoms associated with, and/or reducing secondary recurrences of a non-alcoholic fatty liver disease (NAFLD) and/or any other disorder of the liver, comprising administering to the subject: (i) a sulforaphane precursor, (ii) an enzyme capable of converting the sulforaphane precursor to sulforaphane, (iii) an enzyme potentiator, and (iv) a milk thistle extract or powder.

The present invention provides a composition comprising: (i) sulforaphane or a derivative thereof, and (ii) a milk thistle extract or powder. The present invention also provides a method of treating, preventing, reducing the occurrence of, decreasing the symptoms associated with, and/or reducing secondary recurrences of, a disease or condition associated with the liver, prostate, brain, lung, kidneys, colon, breast, esophagus, pancreas, or ovaries in a subject, comprising administering to the subject: (i) sulforaphane or a derivative thereof, and (ii) a milk thistle extract or powder. The present invention also provides a method of increasing glutathione levels in a subject in need thereof in a subject, comprising administering to the subject, comprising administering to the subject: (i) sulforaphane or a derivative thereof, and (ii) a milk thistle extract or powder. The present invention also provides a method of treating, preventing, reducing the occurrence of, decreasing the symptoms associated with, and/or reducing secondary recurrences of a non-alcoholic fatty liver disease (NAFLD) and/or any other disorder of the liver, comprising administering to the subject: (i) sulforaphane or a derivative thereof, and (ii) a milk thistle extract or powder.

The present invention provides a composition comprising: (i) a broccoli extract or powder, and (ii) milk thistle extract or powder. The present invention also provides a method of treating, preventing, reducing the occurrence of, decreasing the symptoms associated with, and/or reducing secondary recurrences of, a disease or condition associated with the liver, prostate, brain, lung, kidneys, colon, breast, esophagus, pancreas, or ovaries in a subject, comprising administering to the subject: (i) a broccoli extract or powder, and (ii) a milk thistle extract or powder. The present invention also provides a method of increasing glutathione levels in a subject in need thereof in a subject, comprising administering to the subject, comprising administering to the subject: (i) a broccoli extract or powder, and (ii) a milk thistle extract or powder. The present invention also provides a method of treating, preventing, reducing the occurrence of, decreasing the symptoms associated with, and/or reducing secondary recurrences of a non-alcoholic fatty liver disease (NAFLD) and/or any other disorder of the liver, comprising administering to the subject: (i) a broccoli extract or powder, and (ii) a milk thistle extract or powder.

DETAILED DESCRIPTION

Figure 1:
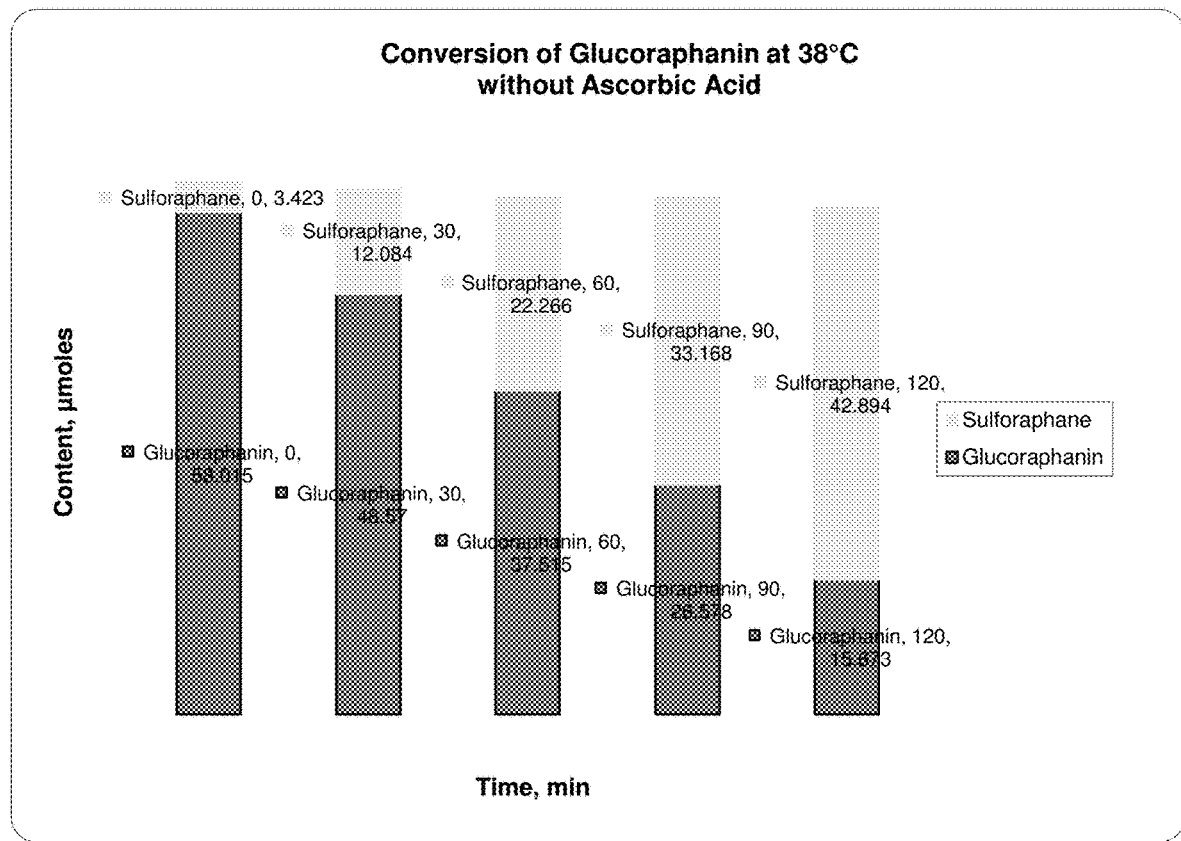
FIG. 1 is a graph showing the conversion of glucoraphanin at 38° C. without ascorbic acid, as described in Example 4.
Figure 2:
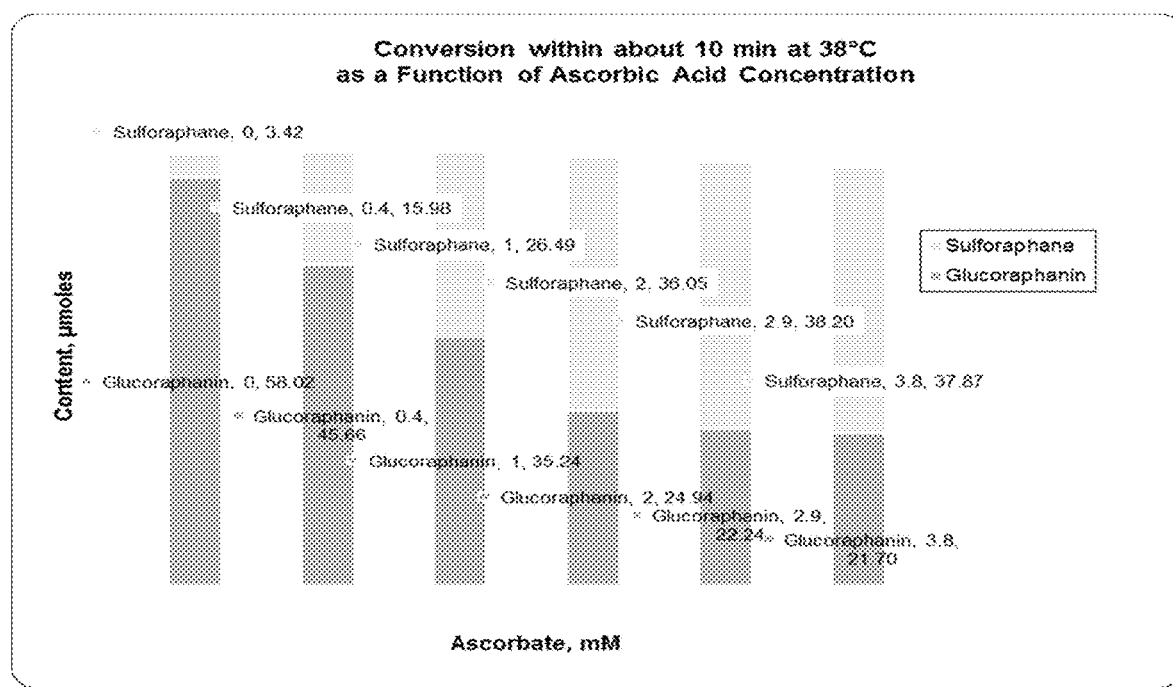
FIG. 2 is a graph showing the conversion within about 10 minutes at 38° C. as a function of ascorbic acid concentration, as described in Example 4.
Figure 3:
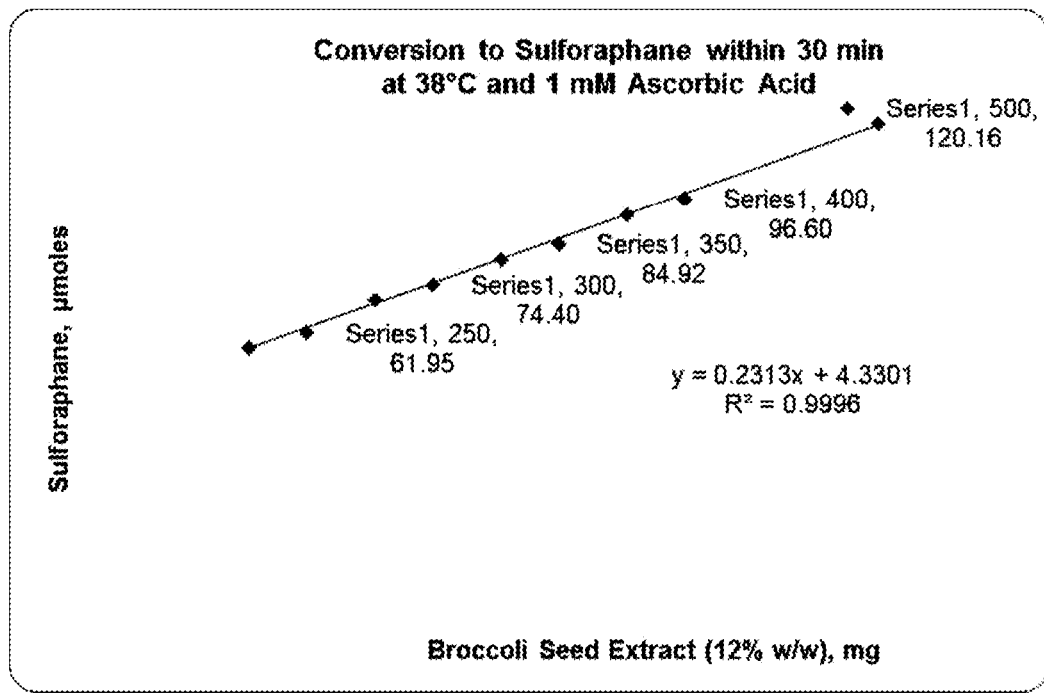
FIG. 3 is a graph showing the conversion to sulforaphane within 30 minutes at 38° C. and 1 mM ascorbic acid, as described in Example 4.

The present invention relates to the combination of a sulforaphane precursor, an enzyme capable of converting the sulforaphane precursor to sulforaphane, an enzyme potentiator, and a milk thistle extract or powder. The present invention also relates to the combination of sulforaphane or a derivative thereof and a milk thistle extract or powder. The present invention also relates to the combination of a broccoli extract or powder and a milk thistle extract or powder. The present invention also relates to the use of milk thistle extract or powder, with a mixture of one or more of the following: sulforaphane precursor, sulforaphane or a derivative thereof, and broccoli extract. The present invention provides compositions relating to these combinations.

The present invention provides methods comprising administering these combinations. In some embodiments, the combination may be administered for treating, preventing, reducing the occurrence of, decreasing the symptoms associated with, and/or reducing secondary recurrences of, a disease or condition associated with the liver, prostate, brain, lung, kidneys, colon, breast, esophagus, pancreas, or ovaries in a subject, comprising administering to the subject. In some embodiments, the combination may be administered for increasing glutathione levels in a subject in need thereof in a subject. In some embodiments, the combination may be administered for treating, preventing, reducing the occurrence of, decreasing the symptoms associated with, and/or reducing secondary recurrences of a non-alcoholic fatty liver disease (NAFLD) and/or any other disorder of the liver in a subject.

Sulforaphane is also known as 1-isothiocyanato-4-methylsulfinylbutane. Derivatives of sulforaphane include, but are not limited to sulfoxythiocarbamate analogues of sulforaphane, 6-methylsulfinylhexyl isothiocyanate (6-HITC), and compounds which comprise the structure of sulforaphane with different side chains and/or various lengths of spacers between the isothiocyanato and sulfoxide groups. Examples of derivatives of sulforaphane include those described in the following references, each of which is incorporated herein by reference: Hu et al., *Eur J Med Chem*, 2013, 64:529-539; Ahn et al., *Proc Natl Acad Sci USA*, 2010, 107(21):9590-9595; and Morimistu et al., *J. Biol. Chem.* 2002, 277:3456-3463, and Baird et al., *Arch Toxicol*, 2011, 85(4):241-272.

In some embodiments, the composition comprises sulforaphane or a derivative thereof, preferably sulforaphane, in an amount of about 1 µg to about 10 g, preferably about 3 µg to about 5 g, preferably about 5 µg to about 1000 mg, preferably about 7 µg to about 750 mg, more preferably about 10 µg to about 500 mg, and most preferably about 100 µg to about 100 mg. In some embodiments, compositions suitable for human use comprise about 1 mg to about 20 mg.

In some embodiments, the methods of the present invention comprise administration of sulforaphane or a derivative thereof to a subject, preferably sulforaphane, in an amount of about 1 µg to about 10 g, preferably about 3 µg to about 5 g, preferably about 5 µg to about 1000 mg, preferably about 7 µg to about 750 mg, more preferably about 10 µg to about 500 mg, and most preferably about 100 µg to about 100 mg. In some embodiments wherein the subject is a human, the method comprises administration of about 1 mg to about 20 mg. In some embodiments, the methods of the present invention comprise administration of sulforaphane or a derivative thereof to a subject, preferably sulforaphane, in an amount of about 0.01 mg/kg to about 0.2 g/kg, preferably about 0.05 µg/kg to about 0.07 g/kg, more preferably about 0.07 µg/kg to about 15 mg/kg, more preferably about 0.1 µg/kg to about 11 mg/kg, and most preferably about 0.2 µg/kg to about 7 mg/kg. In some preferred embodiments wherein the subject is a human, the method comprises administration of about 2 µg/kg to about 2 mg/kg, and more preferably about 0.01 mg/kg to about 0.3 mg/kg. The above amounts may refer to each dosage administration or a total daily dosage. The total daily dosage refers to the total amount of a compound or ingredient which is administered to a subject in a twenty-four hour period.

In some embodiments, the method comprises administration of more than one of a sulforaphane or a derivative thereof. In some embodiments, the compositions comprise more than one of a sulforaphane or a derivative thereof. For example, the methods or composition may comprise both sulforaphane and one or more derivatives thereof, or two or more derivatives. In some embodiments wherein the method or composition comprise more than one of a sulforaphane or a derivative thereof, the above amounts may refer to the amount of each sulforaphane or a derivative thereof, or the total amount of the more than one sulforaphane or derivative thereof.

The term "sulforaphane precursor" refers to any compound, substance or material which can be used to produce sulforaphane. In preferred embodiments, the sulforaphane precursor comprises a compound which can be converted or metabolized to sulforaphane, preferably by an enzyme. In some preferred embodiments, the sulforaphane precursor comprises glucoraphanin. Glucoraphanin is a glucosinolate which is also known as 4-methylsulfinylbutyl glucosinolate and 1-S-[(1E)-5-(methylsulfinyl)-N-(sulfonatooxy) pentanimidoyl]-1-thio-β-D-glucopyranose.

In some embodiments, the composition comprises about 1 μg to about 10 g, preferably about 250 μg to about 5 g, more preferably about 500 μg to about 2000 mg, even more preferably about 1 mg to about 750 mg, even more preferably about 1.5 mg to about 250 mg, even more preferably about 2 mg to about 100 mg, and most preferably about 3 mg to about 75 mg of the sulforaphane precursor, preferably glucoraphanin. In some embodiments, compositions suitable for human use comprise about 3.5 mg to about 50 mg of the sulforaphane precursor, preferably glucoraphanin.

In some embodiments, the method comprises administering the sulforaphane precursor, preferably glucoraphanin to a subject, in an amount of about 1 μg to about 10 g, preferably about 250 μg to about 5 g, more preferably about 500 μg to about 2000 mg, even more preferably about 1 mg to about 750 mg, even more preferably about 1.5 mg to about 250 mg, even more preferably about 2 mg to about 100 mg, and most preferably about 3 mg to about 75 mg. In some embodiments wherein the subject is a human, the method comprises administration of about 3.5 mg to about 50 mg. In some embodiments, the method comprises administering an amount of sulforaphane precursor to a subject in an amount of about 1 μg/kg to about 1000 mg/kg, preferably about 5 μg/kg to about 500 mg/kg, more preferably about 7.5 μg/kg to about 100 mg/kg, even more preferably about 10 μg/kg to about 25 mg/kg, and most preferably about 25 μg/kg to about 10 mg/kg. In some embodiments wherein the subject is a human, the method comprises administration of about 50 μg/kg to about 800 μg/kg. The above amounts may refer to each dosage administration or a total daily dosage.

In some embodiments, the method comprises administration of more than one sulforaphane precursor. In some embodiments, the composition comprises more than sulforaphane precursor. In some embodiments wherein the method or composition comprises more than one sulforaphane precursor, the above amounts may refer to the amount of each sulforaphane precursor, or the total amount of the sulforaphane precursors.

The sulforaphane precursor may be converted or metabolized to sulforaphane. In some embodiments, the sulforaphane precursor is converted to sulforaphane by an enzyme. In some embodiments, the enzyme capable of converting the sulforaphane precursor to sulforaphane comprises a glucosidase enzyme, preferably a thioglucosidase enzyme, and more preferably myrosinase. Myrosinase is also known as thioglucoside glucohydrolase.

In some embodiments, the composition comprises the enzyme in an amount of about 1 pg to about 1 ug, preferably about 50 pg to about 500 ng, and most preferably about 1 ng to about 150 ng. In some embodiments, compositions suitable for human use comprise about 5 ng to about 75 ng of the enzyme.

In some embodiments, the method comprises administering the enzyme, preferably myrosinase, in an amount of about 1 pg to about 1 μg, preferably about 50 pg to about 500 ng, and most preferably about 1 ng to about 150 ng. In some embodiments wherein the subject is a human, the method comprises administration of about 5 ng to about 75 ng of the enzyme. In some embodiments, the method comprises administering the enzyme to a subject in an amount of about 0.02 pg/kg to about 0.02 ug/kg, preferably about 0.7 pg/kg to about 7 ng/kg, and most preferably about 0.02 ng/kg to about 2 ng/kg. In some preferred embodiments wherein the subject is a human, the method comprises administration of about 0.1 ng/kg to about 1 ng/kg. The above amounts may refer to each dosage administration or a total daily dosage.

In some embodiments, the method comprises administration of more than one enzyme capable of converting the sulforaphane precursor to sulforaphane. In some embodiments, the composition comprises more than one enzyme capable of converting the sulforaphane precursor to sulforaphane. In some embodiments wherein the methods or compositions comprise more than one enzyme, the above amounts may refer to the amount of each enzyme, or the total amount of the enzymes.

The present invention also provides for the use of a broccoli extract and/or powder, including but not limited to broccoli seed and sprout extracts and powders. The present invention provides methods of administration of broccoli extract and/or powder, and compositions comprising broccoli extract and/or powder. In some embodiments, the broccoli extract or powder is standardized to contain about 1% to about 75% w/w, more preferably about 2.5% to about 50%, even more preferably about 5% to about 25%, and most preferably about 10% to about 20% of a sulforaphane precursor, preferably glucoraphanin. Examples of broccoli extracts and powders include but are not limited to those described in U.S. Pat. Nos. 5,411,986; 5,725,895; 5,968,505; 5,968,567; 6,177,122; 6,242,018; 6,521,818; 7,303,770, and 8,124,135, each of which is incorporated by reference in its entirety. Powders of broccoli may be obtained, for example, by air drying, freeze drying, drum drying, spray drying, heat drying and/or partial vacuum drying broccoli, preferably broccoli sprouts. In some embodiments, the compositions and methods comprise use of about 1 μg to about 10 g, more preferably about 250 μg to about 5 g, even more preferably about 500 μg to about 1 g, preferably about 600 μg to about 500 mg, more preferably about 750 μg to about 400 mg, and most preferably about 1 mg to about 300 mg of the broccoli extract. In some embodiments, the broccoli extract or powder is present in a composition or administered to a subject in amounts sufficient to provide a sulforaphane precursor or sulforaphane in the amounts described above. In some embodiments, the composition may further comprise an enzyme potentiator, preferably ascorbic acid. In some embodiments, the method may further comprise administration of an enzyme potentiator, preferably ascorbic acid.

The sulforaphane or a derivative thereof, the sulforaphane precursor, and/or the enzyme capable of converting the sulforaphane precursor to sulforaphane may be obtained from any source, including but not limited to one or more plants from the Brassicaceae (also known as Cruciferae) family. Examples of plants from the Brassicaceae family include, but are not limited to, the following: broccoli, Brussels sprouts, cauliflower, cabbage, horseradish, parsnip, radish, wasabi, watercress, and white mustard. In some preferred embodiments, sulforaphane precursor, preferably glucoraphanin, and the enzyme, preferably myrosinase, are obtained from broccoli, broccoli sprouts, or broccoli seeds. The sulforaphane precursor and the enzyme may be obtained from the same source or from different sources. In some embodiments, both the sulforaphane precursor and the enzyme may be obtained from an extract or powder from these plants, preferably a broccoli seed or sprout extract or powder.

The present invention provides for the use of an enzyme potentiator. Enzyme potentiators may be used to enhance the activity of the enzyme that is capable of converting the sulforaphane precursor to sulforaphane. In some embodiments, the enzyme potentiator comprises an enzyme co-factor, preferably ascorbic acid. Ascorbic acid, also known as ascorbate or vitamin C, can potentiate the activity of myrosinase. In some embodiments, without an enzyme potentiator such as ascorbic acid, the conversion reaction to sulforaphane may be too slow to occur in the location needed for peak absorption. The enzyme potentiator may be obtained from a natural source, or it may be produced synthetically.

In some embodiments, the compositions may comprise about 1 mg to about 500 mg, preferably about 1 mg to about 250 mg, and most preferably about 1 mg to about 125 mg of the enzyme potentiator. In some preferred embodiments, compositions suitable for human use comprise about 1 mg to about 50 mg of the enzyme potentiator.

In some embodiments, the method of the present invention comprises administration of an enzyme potentiator, preferably ascorbic acid, in an amount of about 1 mg to about 500 mg, preferably about 1 mg to about 250 mg, and most preferably about 1 mg to about 125 mg. In some preferred embodiments wherein the subject is a human, the method comprises administration of about 1 mg to about 50 mg. In some embodiments, the method of the present invention comprises administration of the enzyme potentiator, preferably ascorbic acid, in an amount of about 0.01 mg/kg to about 3 mg/kg, and most about 0.02 mg/kg to about 2 mg/kg. In some preferred embodiments wherein the subject is a human, the method comprises administration of about 0.02 mg/kg to 0.7 mg/kg of the enzyme potentiator. The above amounts may refer to each dosage administration or a total daily dosage.

In some embodiments, the method comprises administration of more than one enzyme potentiator. In some embodiments, the composition comprises more than one an enzyme potentiator. In some embodiments wherein the method or composition comprise more than one enzyme potentiator, the above amounts may refer to the amount of each enzyme potentiator, or the total amount of the enzyme potentiators.

The present invention further comprises the use of a milk thistle extract or powder. Milk thistle belongs to the species *Silybum marianum*. Milk thistle comprises a number of components or fractions having biological activity. An active fraction of milk thistle is silymarin, which comprises a number of constituents. Examples of constituents of silymarin include, but are not limited to: silibinin (also known as silybin or silibin), isosilibinin, silichristin, silydianin, and kvercetin, dehydrosilybin, deoxysilycistin, deoxysilydianin, silandrin, silybinome, silyhermin and neosilyhermin. Isomers of silibinin include Silybinin A (or Silibinin A) and Silybinin B (or Silbinin B). In preferred embodiments, the milk thistle extract or powder comprises silymarin.

In some embodiments, the compositions and methods of the present invention may comprise the use of one or more derivatives of silymarin, instead of or in addition to a milk thistle extract or powder. Derivatives of silymarin constituents include any modified forms of the above compounds, including but not limited to, 7-O- and 23-O-acyl derivatives, and analogues. Examples of derivatives of silymarin constituents include, but are not limited to 2,3-dehydrosilybin (DHS); 7-O-methylsilybin; 7-O-galloylsilybin; 7,23-disulphatesilybin (DSS); 7-O-palmitoylsilybin; and 23-O-palmitoylsilybin. Examples of derivatives include those described in the following references, each of which is incorporated herein by reference in its entirety: Agarwal et al. *PLOS ONE,* 2013, 8(3):e60074; GB 2167414; and CA1337124. In some embodiments, the compositions and methods of the present invention may comprise the use of silymarin or silibinin in a purified form or silymarin or silibinin produced synthetically, instead of or in addition to a milk thistle extract or powder.

In some embodiments, the milk thistle extract or powder may be used. In preferred embodiments, the milk thistle extract comprises silymarin. In preferred embodiments, the milk thistle extract comprises silibinin. In some embodiments, the milk thistle extract or powder is standardized to contain about 25% to about 95%, preferably about 50% to about 90%, and more preferably about 55% to about 85% silymarin. In some embodiments, the milk thistle extract or powder is standardized to contain about 5% to about 75%, preferably about 10% to about 60%, more preferably about 15% to about 50%, and most preferably about 20% to about 35% of silibinin. Examples of milk thistle extract include, but are not limited to, those described in U.S. Pat. Nos. 6,555,141; 6,863,906; 7,563,779; WO200908006; EP2020238; WO2009043671; EP1584240; and WO2011076154, each of which is incorporated by reference in its entirety. Powders of milk thistle may be obtained, for example, by air drying, freeze drying, drum drying, spray drying, heat drying and/or partial vacuum drying milk thistle.

In some embodiments, the compositions and methods comprise use of about 1.25 mg to about 15 grams, preferably about 5 mg to about 10 grams, and most preferably about 10 mg to about 7.5 grams of milk thistle extract. In some preferred embodiments wherein the composition is suitable for human use, the composition comprises about 25 mg to about 5 grams of the milk thistle extract. In some embodiments, the composition comprises about 0.75 mg to about 15 grams, preferably about 3 mg to about 7 grams, more preferably about 7 mg to about 5 grams, and most preferably about 15 mg to about 3.5 grams of silymarin. In some preferred embodiments wherein the composition is suitable for human use, the composition comprises about 50 mg to about 200 mg of silymarin. In some embodiments, the composition comprises about 0.3 mg to about 5 grams, preferably about 1.5 mg to about 3 grams, more preferably about 3 mg to about 2 grams, and most preferably about 7 mg to about 1.5 grams of silibinin. In some preferred embodiments wherein the composition is suitable for human use, the composition comprises about 30 mg to about 90 mg of silibinin.

In some embodiments, the method comprises administration of silymarin in an amount of about 1 µg/kg to about 75 mg/kg, preferably about 2.5 µg/kg to about 50 mg/kg, more preferably about 5 µg/kg to about 25 mg/kg, more preferably about 10 µg/kg to about 15 mg/kg, and most preferably about 15 µg/kg to about 10 mg/kg. In some preferred embodiments wherein the subject is a human, the method comprises administration of about 1 mg/kg to about 3 mg/kg of silymarin. In some embodiments, the method comprises administration of silibinin in an amount of about 0.5 µg/kg to about 50 mg/kg, preferably about 1 µg/kg to about 35 mg/kg, more preferably about 2.5 µg/kg to about 25 mg/kg, more preferably about 5 µg/kg to about 10 mg/kg, and most preferably about 7.5 µg/kg to about 5 mg/kg. In some preferred embodiments wherein the subject is a human, the method further comprises administration of about 300 µg/kg to about 2 mg/kg of silibinin. In embodiments wherein a derivative of a silymarin constituent are used, the methods and compositions may comprise the derivative in an amount of about 0.75 mg to about 15 grams, preferably about 3 mg to about 7 grams, more preferably about 7 mg to about 5 grams, and most preferably about 15 mg to about 3.5 grams. In some preferred embodiments wherein the composition is suitable for human use, the compositions comprise about 50 mg to about 200 mg of the derivative of a silymarin constituent. The above amounts may refer to each dosage administration or a total daily dosage.

In some embodiments, S-adenosylmethionine may be used in place of, or in addition to, the milk thistle extract, silymarin and/or silibinin.

The methods of the present invention may further comprise administration of one or more additional components. The compositions of the present invention may further comprise one or more additional components. The additional components may include active pharmaceutical ingredients, nutritional supplements, and nutritional extracts. Examples of additional components include, but are not limited, quercetin or a derivative thereof, an aminosugar such as glucosamine, a glycosaminoglycan such as chondroitin, avocado/soybean unsaponifiables, vitamins such as vitamin K2, coffee fruit, magnesium, ursolic acid, proanthocyanidins, alpha- and beta-glucans, curcumin, phytosterols, phytostanols, and S-adenosylmethionine (SAMe). These additional components may be present in cranberry (*Vaccinium macrocarpon*) extract (proanthocyanidins, quercetin, and ursolic acid), turmeric (*Curcuma longa*), medicinal mushroom extract such as shiitake (*Lentinus edodes*), maitake (*Grifola frondosa*) mushroom extracts, and reishi (*Ganoderma lucidum*) mushroom extract.

In some embodiments, the ratio of silymarin to sulforaphane or a derivative of is about 1:1 to about 75:1, more preferably about 2:1 to about 50:1, more preferably about 2.5:1 to about 25:1, even more preferably about 5:1 to about 15:1, and most preferably about 6:1 to about 9:1. In some embodiments, the ratio of silibinin to sulforaphane or a derivative of is about 1:2 to about 35:1, more preferably about 1:1 to about 25:1, more preferably about 1:1 to about 15:1, even more preferably about 2:1 to about 10:1, and most preferably about 2:1 to about 5:1. In some embodiments, the ratio of silymarin to sulforaphane precursor of is about 1:5 to about 50:1, preferably about 1:2 to about 25:1, more preferably about 1:1 to about 10:1, more preferably about 1.5:1 to about 5:1, and most preferably about 1:1 to about 4:1. In some embodiments, the ratio of silibinin to sulforaphane precursor is about 1:5 to about 50:1, preferably about 1:2 to about 25:1, preferably 1:1 to about 20:1, and most preferably about 1:1 to about 13:1.

In some embodiments, the composition comprises a unit dosage form, including but not limited to pharmaceutical dosage forms suitable for oral, rectal, intravenous, subcutaneous, intramuscular, transdermal, transmucosal, and topical. In some preferred embodiments, the composition comprises an orally administrable dosage form or a rectally administrable dosage form. Examples of orally administrable dosage forms include, but are not limited to a tablet, capsule, powder that can be dispersed in a beverage, a liquid such as a solution, suspension, or emulsion, a soft gel/chew capsule, a chewable bar, or other convenient dosage form known in the art. In preferred embodiments, the composition comprises a tablet, capsule, or soft chewable treat. The orally administrable dosage forms may be formulated for immediate release, extended release or delayed release.

In some embodiments, at least the sulforaphane precursor, the enzyme, and the enzyme potentiator are provided in a dosage form which allows for the release in an area of the gastrointestinal tract having a pH of at least 4 and preferably at least 5, such as the small intestine, preferably the duodenum. In some embodiments, at least the sulforaphane or derivative thereof and/or the broccoli extract or powder are provided in a dosage form which allows for the release in an area of the gastrointestinal tract having a pH of at least 4 and preferably at least 5, such as the small intestine, preferably the duodenum. In some embodiments, the milk thistle extract or powder and/or any optional additional components are also released in an area of the gastrointestinal tract having a pH of at least 4 and preferably at least 5, such as the small intestine, preferably the duodenum. The small intestine includes the duodenum, jejunum, and ileum.

In some embodiments, each of these components (i.e., sulforaphane precursor, enzyme, enzyme potentiator, sulforaphane or a derivative thereof, broccoli extract or powder, milk thistle extract or powder, and/or additional components) are released simultaneously or concomitantly (i.e., within a short period of time of each other). This provides benefits over glucoraphanin-containing compositions formulated to release the glucoraphanin in an area of the gastrointestinal tract having a pH below 4, such as the stomach. In low pH environments such as this, the acidic environment may divert conversion of sulforaphane precursor to other, physiologically inactive end products, such as sulforaphane nitrile and epithionitrile.

In some embodiments, the compositions may comprise orally administrable compositions which comprise gastroprotective formulations, including enteric coated dosage forms or any dosage form which is resistant to degradation in an area of the gastrointestinal tract having pH below 4, such as the stomach. For example, the orally administrable composition may comprise a tablet or capsule comprising an enteric coating. The enteric coating may comprise materials including, but not limited to cellulose acetate phthalate, hydroxypropyl methylcellulose phthalate, polyvinyl acetate phthalate, methacrylic acid copolymer, methacrylic acid: acrylic ester copolymer, hydroxypropyl methylcellulose acetate succinate, hydroxypropyl methylcellulose trimellitate, shellac, cellulose acetate trimellitate, carboxymethylethylcellulose, and mixtures thereof. The enteric coating may comprise any suitable enteric polymers known in the art. In some embodiments, one or more of the components in the composition may be embedded in a matrix of enteric polymers. In some embodiments, the orally administrable compositions comprise a capsule that dissolves slowly in gastric acid and travels to the small intestine, such as DRCAPS™ acid resistant capsules, which are marketed by CAPSUGEL® or any other acid resistant capsules.

In the most preferred form, the orally administrable composition is surrounded by a coating that does not dissolve unless the surrounding medium is at a pH of at least 4, and more preferably at least 5. Alternatively, a coating may be employed which controls the release by time, as opposed to pH, with the rate adjusted so that the components are not released until after the pH of the gastrointestinal tract has risen to at least 4, and more preferably at least 5. Thus, a time-release formulation may be used to prevent gastric presence of the sulforaphane precursor, the enzyme capable of converting the sulforaphane precursor to sulforaphane, and the enzyme potentiator, or of the sulforaphane. The coating layer(s) may be applied onto orally administrable composition using standard coating techniques. The enteric coating materials may be dissolved or dispersed in organic or aqueous solvents. The pH at which the enteric coat will dissolve can be controlled by a polymer, or combination of polymers, selected and/or ratio of pendant groups. For example, dissolution characteristics of the polymer film can be altered by the ratio of free carboxyl groups to ester groups. Enteric coating layers also contain pharmaceutically acceptable plasticizers such as triethyl citrate, dibutyl phthalate, triacetin, polyethylene glycols, polysorbates or other plasticizers. Additives such as dispersants, colorants, anti-adhering and anti-foaming agents may also be included.

The compositions may contain one or more non-active pharmaceutical ingredients (also known generally as "excipients"). Non-active ingredients, for example, serve to solubilize, suspend, thicken, dilute, emulsify, stabilize, preserve, protect, color, flavor, and fashion the active ingredients into an applicable and efficacious preparation that is safe, convenient, and otherwise acceptable for use. The excipients are preferably pharmaceutically acceptable excipients. Examples of classes of pharmaceutically acceptable excipients include lubricants, buffering agents, stabilizers, blowing agents, pigments, coloring agents, flavoring agents, fillers, bulking agents, fragrances, release modifiers, adjuvants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers and mixtures thereof.

In some embodiments, the combination of (i) a sulforaphane precursor, preferably glucoraphanin, (ii) an enzyme capable of converting the sulforaphane precursor to sulforaphane, preferably a glucosidase enzyme, more preferably a thioglucosidase enzyme, and most preferably myrosinase, (iii) an enzyme potentiator, preferably an enzyme co-factor, more preferably ascorbic acid, and (iv) milk thistle extract or powder demonstrates a synergistic effect. In some embodiments, the combination of sulforaphane (or a derivative thereof) and a milk thistle extract or powder demonstrates a synergistic effect. Synergy refers to the effect wherein a combination of two or more components provides a result which is greater than the sum of the effects produced by the agents when used alone. In preferred embodiments, the synergistic effect is greater than an additive effect. In some embodiments, the combination of a sulforaphane precursor, an enzyme capable of converting the sulforaphane precursor to sulforaphane, an enzyme potentiator, and a milk thistle extract or powder has a statistically significant, greater effect compared to: (i) each component alone, (ii) the combination of sulforaphane precursor and the enzyme alone; and/or (iii) the combination of sulforaphane precursor, the enzyme, and the enzyme potentiator alone.

In preferred embodiments, the combination of the sulforaphane precursor, the enzyme, the enzyme potentiator, and a milk thistle extract or powder demonstrates synergy by having a statistically significant and/or greater than additive effect compared to the sulforaphane precursor alone and the milk thistle extract or powder alone. In some embodiments, the combination of glucoraphanin, myrosinase, ascorbic acid, and silymarin has a synergistic effect compared to the combination of glucoraphanin, myrosinase, ascorbic acid alone; and compared to silymarin alone. In some embodiments, the combination of glucoraphanin, myrosinase, ascorbic acid, and silibinin has a synergistic effect compared to the combination of glucoraphanin, myrosinase, ascorbic acid alone; and compared to silibinin alone.

In some embodiments, the combination of a sulforaphane (or a derivative thereof) and a milk thistle extract or powder has a statistically significant and/or greater than additive effect than: (i) sulforaphane (or a derivative thereof) alone, and/or (ii) a milk thistle extract or powder alone. In some embodiments, the combination of sulforaphane and silymarin has a synergistic effect compared to sulforaphane alone, and silymarin alone. In some embodiments, the combination of sulforaphane and silibinin has a synergistic effect compared to sulforaphane alone, and silibinin alone.

In some embodiments, the combination of broccoli extract or powder and a milk thistle extract or powder has a statistically significant and/or greater than additive effect than: (i) broccoli extract or powder alone, and/or (ii) a milk thistle alone. In some embodiments, the combination of broccoli extract or powder and silymarin has a synergistic effect compared to broccoli extract or powder alone, and silymarin alone. In some embodiments, the combination of broccoli extract or powder and silibinin has a synergistic effect compared to broccoli extract or powder alone, and silibinin alone.

The present invention provides methods of use, including methods of administration to a subject in need thereof. In some embodiments, the method comprises administration of the combination of a sulforaphane precursor, an enzyme capable of converting the sulforaphane precursor to sulforaphane, an enzyme potentiator, and a milk thistle extract or powder. In some embodiments, the method comprises administration of the combination of a sulforaphane or a derivative thereof and a milk thistle extract or powder. In some embodiments, the method comprises administration of the combination of a broccoli extract or powder and a milk thistle extract or powder.

In some embodiments, the method relates to treating, preventing, reducing the occurrence of, decreasing the symptoms associated with, and/or reducing secondary recurrences of, a disease or condition associated with the liver, genitourinary system (including prostate, breast, and ovaries), brain, lung, kidneys, colon, esophagus, pancreas, or hematopoietic system in a subject, comprising administering to the subject. The methods may be useful in reducing damage of slowing damage to tissues and organs, such as the liver, genitourinary system (including prostate, breast, and ovaries), brain, lung, kidneys, colon, esophagus, and pancreas. In some embodiments, the method relates to increasing glutathione levels in a subject in need thereof in a subject. The method may also be useful in treating, preventing, decreasing the symptoms associated with, and/or reducing secondary recurrences of diseases or conditions associated with low levels of glutathione. Examples of such diseases and conditions include, but are not limited to, non-alcoholic fatty liver disease (NAFLD), cancer (such as cancer of the liver, lung, prostate, colon, breast, brain, ovaries, esophagus, pancreas, nasopharynx, osteosarcoma), leukemia, cystic fibrosis, HIV, glutathione synthetase deficiency, Alzheimer's disease, Parkinson's disease, Huntington's disease, amyotrophic lateral sclerosis, Friedreich's ataxia, multiple sclerosis, fibromyalgia, chronic fatigue, autism, diabetes, hepatotoxicity, and toxicity due to environmental factors.

In some embodiments, method relates to treating, preventing, reducing the occurrence of, decreasing the symptoms associated with, and/or reducing secondary recurrences of a non-alcoholic fatty liver disease (NAFLD) and/or any other disorder of the liver in a subject. In some embodiments, the methods relate to ameliorating or reducing the deleterious effects of NAFLD.

In some embodiments, the methods relate to providing a beneficial effect on biomarkers, and treating, preventing, reducing the occurrence of, decreasing the symptoms associated with abnormal levels of these biomarkers. Examples of such biomarkers include, but are not limited to NADPH-dependent enzymes, thioredoxin (TXN), thioredoxin reductase-1 (Txnrd-1), glutamate-cysteine ligase subunit (GCLC), sulfotransferase 1A1 (SULT1A1), heme oxygenase-1 (HMOX1), glutathione peroxidase-3 (GPx-3), glutathione S-transferase theta 2 (GSTT2), microsomal glutathione S-transferase 1 (MGST1), aldehyde oxidase (AOX1), aldo-keto reductase 1B8 (Akr1b8), flavin-containing monooxygenase 2 (FMO2), Fc receptor region receptor III (Fcgr3), tryptase beta 1 (TPSB1), mast cell protease-6 (Mcpt6), neurexin-1-alpha (NRXN-1), microphthalmia-associated transcription factor (MITF), type II iodothyronine deiodinase (DIO2), angiopoietin-14 (Angpt14), cluster of differentiation (CD36), and Ntel. Diseases or conditions associated with elevated or abnormal levels of these biomarkers include, but are not limited to cancer, pulmonary and central nervous system tuberculosis, multiple sclerosis, Crohn's disease, atherosclerosis, osteoarthritis, asthma, stroke, emphysema, diabetic nephropathy, chronic histiocytic intervillositis of the placenta, hypertension, abdominal aortic aneurysm, inflammatory bowel disease, chronic rhinosinusitis, coronary artery disease, and kidney disease.

In some embodiments, the method comprises administering to a subject in need thereof a combination of sulforaphane and a milk thistle extract or powder. In some embodiments the method comprises administering to a subject in need thereof a combination of broccoli extract or powder and a milk thistle extract or powder. In some preferred embodiments, the method comprises administering to the subject a combination of glucoraphanin, myrosinase, ascorbic acid, and a milk thistle extract or powder. In preferred embodiments, the combinations demonstrate a synergistic effect in the methods of the present invention.

In preferred embodiments, one or more components of the combinations (for example, the sulforaphane precursor, the enzyme capable of converting the sulforaphane precursor to sulforaphane, the enzyme potentiator, the milk thistle extract or powder; or the sulforaphane or derivative thereof and the milk thistle extract or powder; or the broccoli extract or powder and the milk thistle extract or powder) are administered together in one composition or dosage form, or separately, preferably within a period in which their therapeutic properties overlap. In some embodiments, the components of the combinations may be administered in two or more orally administrable compositions or dosage forms. For example, in some embodiments, the sulforaphane precursor, the enzyme capable of converting the sulforaphane precursor to sulforaphane, and the enzyme potentiator are administered in one orally administrable dosage form, while the a milk thistle extract or powder are administered in one or more separate or additional orally administrable dosage form(s). In preferred embodiments, the components of the combination are administered in one dosage form.

In some embodiments, the combination may be administered at a frequency of 1 to 10 times daily, preferably 1 to 5 times daily, more preferably 1 to 3 times daily, and most preferably 1 time daily.

The dosages disclosed in this application refer generally to dosages suitable for humans. Dosage calculations can be determined by those of skilled in the art by evaluating body weight, surface area, metabolic rate, and species differences.

The term "subject" refers to any animal, including mammals and birds. Mammals include, but are not limited to, humans, dogs, cats, horses, cows, camels, elephants, lions, tigers, bears, seals, and rabbits. In preferred embodiments, the subjects comprise mammals that are not consumed as food, such as humans, cats, and dogs.

EXAMPLES

Example 1

The following is an exemplary formulation:
Glucoraphanin-containing broccoli extract (about 12% w/w), 50 mg to 5 g
Myrosinase-containing freeze-dried broccoli sprout powder, 25 mg to 500 mg
Ascorbic acid, 5 mg to 500 mg
Milk thistle extract (about 20% to 35% w/w silibinin), 25 mg to 5 g Example 2

A Hydrophobic Interaction Chromatographic (HILIC) method was developed, comprising the following conditions:
Column: Waters BEH Amide, 1.7-μm particle size; 2.1 mm×100 mm
Mobile Phase: 20% 10 mM Ammonium Acetate, pH 5.0; 80% Acetonitrile;
Separation mode: isocratic
Column Temperature: 70° C.
Flow Rate: 0.7 mL/min
The above conditions allow separation of five typical Brassicaceae glucosinolates, including the sulforaphane precursor, glucoraphanin.

Example 3

Consumption of Glucoraphanin as a Function of the Ascorbic Acid Concentration.

About 250 mg of broccoli seed extract containing about 12% (w/w) glucoraphanin were subjected to hydrolysis by a fixed concentration of broccoli sprout-derived myrosinase in the presence of variable concentration of ascorbic acid, ranging from 0 to 600 moles/Liter. The reaction mixtures were thermostated at 38° C.; aliquots were withdrawn every 15 minutes for 60 minutes, and concentration of glucoraphanin determined chromatographically. The rate of glucoraphanin consumption was interpreted as the rate its conversion to sulforaphane. Graphical representation of glucoraphanin content reduction as a function of increasing ascorbic acid concentration results in a series of linear plots; the slopes of the linear regression lines reflect the rate of glucoraphanin consumption, in moles/minute. It is apparent that in the presence of 600 μmoles/Liter concentration of ascorbic acid, the reaction rate increased 13-fold relative to that which proceeded in the absence of modulatory effects of ascorbic acid.

| Time, min | | | | Content of Ascorbic Acid | | | | |
| --- | --- | --- | --- | --- | --- | --- | --- | --- |
| | 0 μM | 50 μM | 125 μM | 250 μM | 250 μM Filtered | 400 μM | 600 μM | |
| 0 | 93.36 | 93.36 | 93.36 | 93.36 | 93.36 | 93.36 | 93.36 | μmoles |
| 15 | 92.24 | 89.20 | 84.52 | 80.95 | 86.31 | 78.32 | 75.02 | GR |
| 30 | 90.71 | 84.24 | 75.92 | 69.06 | 79.44 | 62.78 | 55.66 | |
| 45 | 89.44 | 80.30 | 68.09 | 57.63 | 71.94 | 47.67 | 37.50 | |

-continued

| | Content of Ascorbic Acid | | | | | | |
|---|---|---|---|---|---|---|---|
| Time, min | 0 μM | 50 μM | 125 μM | 250 μM | 250 μM Filtered | 400 μM | 600 μM |
| 60 | 87.79 | 76.36 | 59.41 | 45.76 | 65.18 | 33.15 | 22.09 |
| Slope | −0.09293 | −0.28599 | −0.56217 | −0.79012 | −0.47140 | −1.00714 | −1.20029 μmol/min |
| Intercept | 93.496 | 93.271 | 93.123 | 93.053 | 93.386 | 93.270 | 92.734 μmol |

Example 4

Equimolar Conversion of Glucoraphanin to Sulforaphane.

A two-part experiment was conducted to further elucidate the role of ascorbic acid in modulating myrosinase activity. All solutions were prepared in 20 mM Tris-buffered saline, at pH 7.5, previously identified as an optimal for myrosinase activity; each sample tube had 100 mg of freeze-dried broccoli powder accurately weighed in as a source of myrosinase. Experiment was conducted at 38° C. for 2 hours, with sample aliquots removed in 30-minute increments, and both glucoraphanin and sulforaphane content assessed by HPLC. A strongly acidic "stop" solution was utilized to instantaneously inhibit further myrosinase activity in the removed aliquots. A control sample contained no ascorbic acid, and the enzymatic conversion proceeded unassisted by a co-factor.

PART 1. In the presence of the fixed concentration of ascorbic acid, 1 mmol/Liter, an increasing amount of broccoli seed extract (about 12% glucoraphanin, w/w) was added, ranging from 250 mg to 500 mg.

PART 2. While keeping the amount of broccoli seed extract fixed at 250 mg, the concentration of ascorbic acid was varied from 0.4 mmol/Liter to 3.8 mmol/Liter.

The table below presents glucoraphanin and sulforaphane expressed in moles. It is apparent that within the first 30 minutes in almost all the reaction mixtures, conversion of glucoraphanin to sulforaphane was complete. However, careful examination of the enzymatic conversion occurring in the control sample, without the stimulating effects of ascorbic acid, reveals an equimolar conversion of glucoraphanin to sulforaphane, i.e., the amount of glucoraphanin consumed results in the equivalent amount of sulforaphane produced.

| | Glucoraphanin, μmoles | | | | | Sulforaphane, μmoles | | | | |
|---|---|---|---|---|---|---|---|---|---|---|
| Time, min | 0 | 30 | 60 | 90 | 120 | 0 | 30 | 60 | 90 | 120 |
| GR 250 mg AA 0.0 mM | 58.02 | 48.57 | 37.52 | 26.58 | 15.67 | 3.42 | 12.08 | 22.27 | 33.17 | 42.89 |
| GR 250 mg AA 1.0 mM | 40.07 | 1.56 | | | | 21.51 | 61.95 | 60.20 | 60.04 | 58.25 |
| GR 300 mg AA 1.0 mM | 49.31 | 1.01 | | | | 24.18 | 74.40 | 73.04 | 72.19 | 70.56 |
| GR 350 mg AA 1.0 mM | 61.41 | | | | | 25.00 | 84.92 | 84.02 | 83.19 | 80.02 |
| GR 400 mg AA 1.0 mM | 71.35 | | | | | 26.71 | 96.60 | 95.38 | 93.39 | 91.16 |
| GR 500 mg AA 1.0 mM | 89.41 | | | | | 33.52 | 120.16 | 118.45 | 116.45 | 112.34 |
| GR 250 mg AA 0.4 mM | 45.66 | | | | | 15.98 | 62.06 | 61.01 | 60.88 | 58.90 |
| GR 250 mg AA 1.0 mM | 35.24 | | | | | 26.49 | 62.19 | 60.62 | 60.41 | 59.10 |
| GR 250 mg AA 2.0 mM | 24.94 | | | | | 36.05 | 60.85 | 59.78 | 59.65 | 58.08 |
| GR 250 mg AA 2.9 mM | 22.24 | | | | | 38.20 | 59.95 | 59.34 | 58.77 | 56.99 |
| GR 250 mg AA 3.8 mM | 21.70 | | | | | 37.87 | 58.77 | 57.79 | 58.41 | 56.17 |

In the Part 2 of the experiment, the modulatory effect of the increasing concentration of ascorbic acid on the activity of myrosinase was assessed. An initial, apparently linear, increase in myrosinase-promoted conversion of glucoraphanin to sulforaphane is observed to about 2 mmol/L of ascorbic acid concentration, followed subsequently by a considerable leveling off.

Finally, examination of sulforaphane yield of after 30 minutes within the PART 1 of the experiment, reveals that in the presence of 1 mmol/Liter of ascorbic acid, the fixed amount of myrosinase contained in 100 mg of freeze-dried broccoli sprout powder is capable of generating at least 200 moles of sulforaphane, in a predictably linear fashion. FIGS. 1, 2, 3, and 4 demonstrate the results of this study.

Example 5

Conversion of Glucoraphanin to Sulforaphane in the Presence of Simulated Intestinal Fluid.

Figure 4:
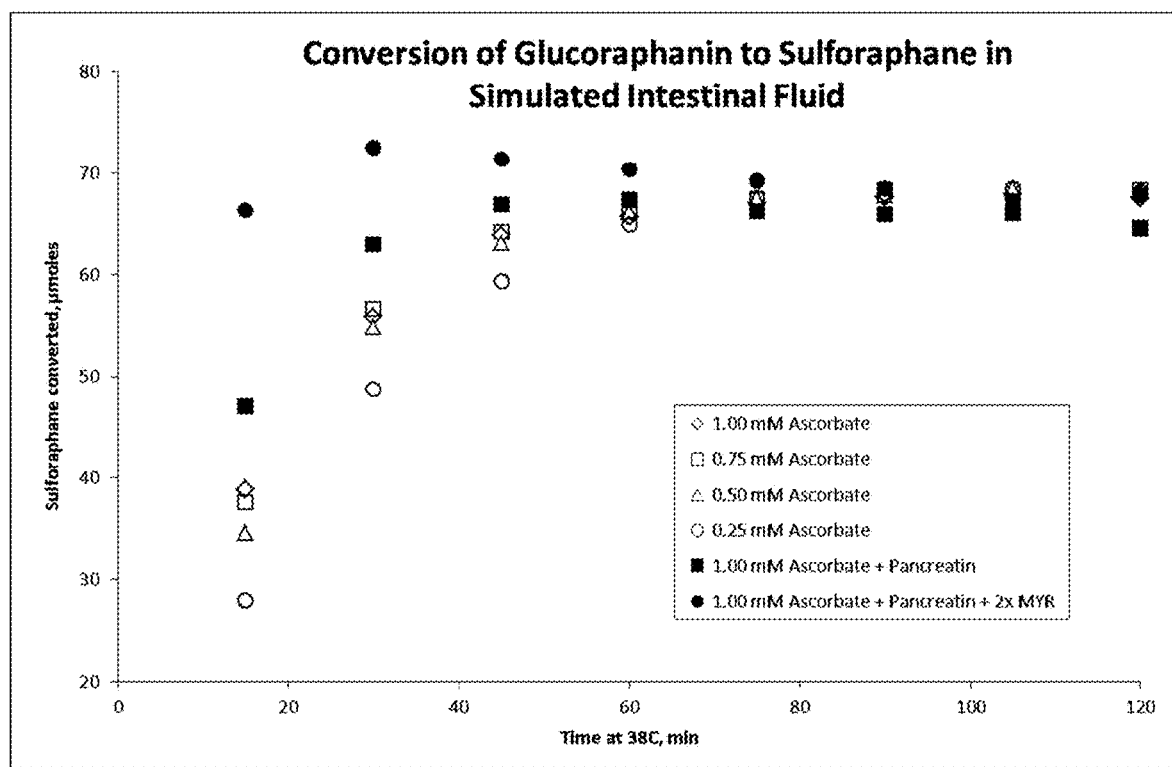
FIG. 4 is a graph showing the conversion of glucoraphanin to sulforaphane in simulated intestinal fluid, as described in Example 5.

Simulated Intestinal Fluid (SW) powder, a commercially supplied concentrate closely approximating the human intestinal content in terms of composition, pH and ionic strength, was used. The experiment utilized a USP Dissolution Apparatus 2 (paddles), where into six dissolution vessels 500 mL of Simulated Intestinal Fluid was dispensed, along with 150 mg of freeze-dried broccoli sprout powder as a source of myrosinase. In vessels 1-4, the concentration of ascorbic acid was varied from 0.25 to 1.00 mmol/Liter; in vessel 5, in addition to 1 mmol/Liter ascorbic acid, 3.125 g of pancreatin (8×USP) was suspended; in vessel 6, in addition to 1 mmol/Liter ascorbic acid, and 3.125 g of pancreatin (8×USP), a doubled amount of freeze-dried broccoli sprout powder (300 mg) was added. After vessels were brought to 38° C., 250 mg of glucoraphanin-rich (12%, w/w) broccoli seed extract was added to each, and the resulting suspensions were stirred at 75 RPM for 2 hours. Aliquots were withdrawn every 15 minutes, and assayed for sulforaphane. FIG. 4 shows direct correlation between larger yield of sulforaphane and higher concentrations of ascorbic acid, especially at the earlier stages of the experiment.

Example 6

The following study was conducted to determine the effect of the combination of sulforaphane and silibinin on glutathione levels. Glutathione plays an important role in the body, as it can serve as an antioxidant, detoxifier, and immunity enhancer. Decreased levels of glutathione can cause a patient to be susceptible to oxidative stress, illness, and cancer. Therefore, an increase in glutathione levels is a beneficial effect.

Figure 5:
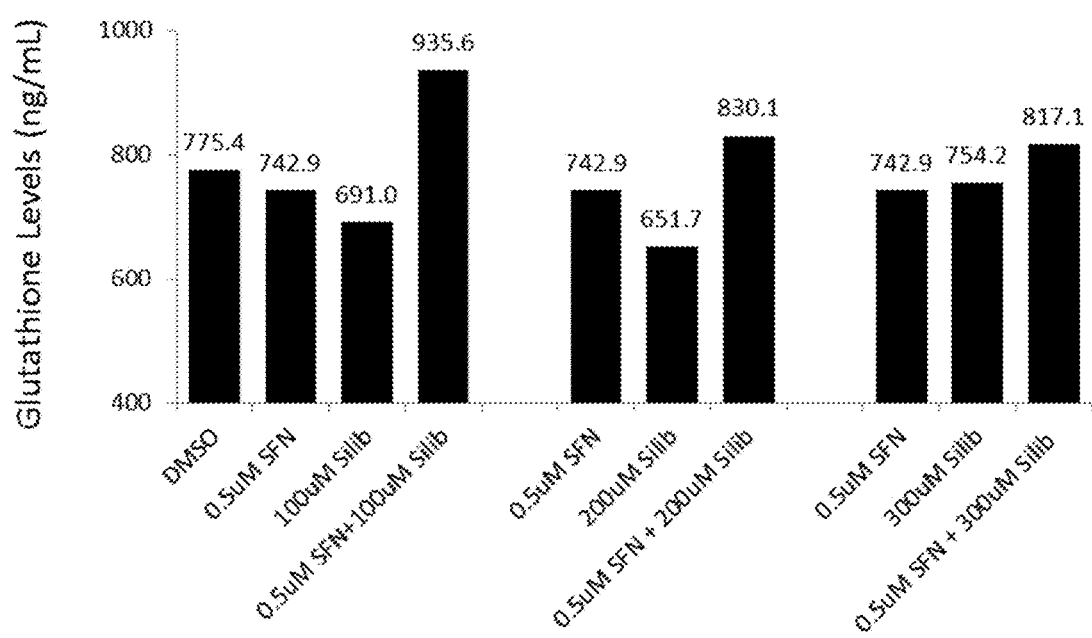
FIG. 5 is a graph showing the results of the experiment described in Example 6.
Figure 6:
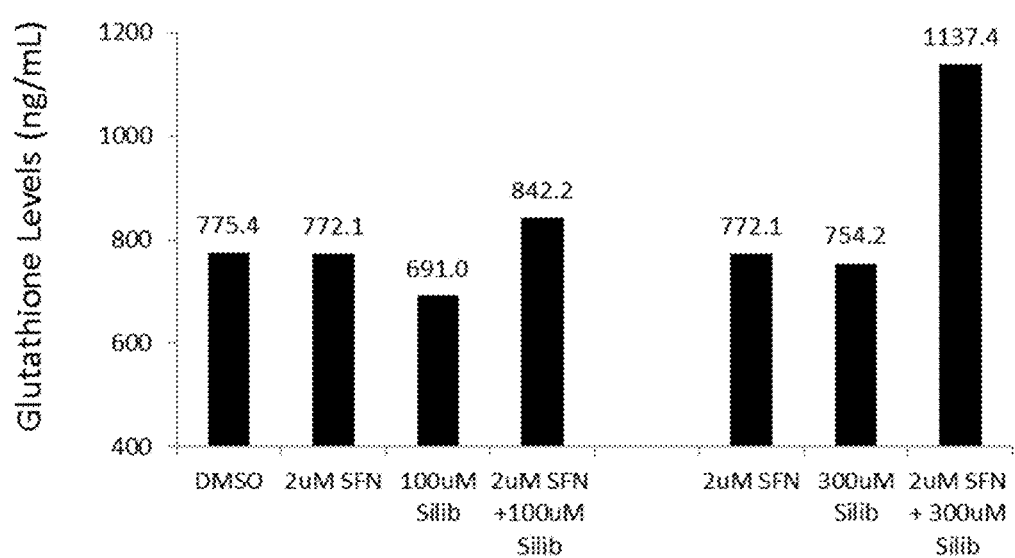
FIG. 6 is a graph showing the results of the experiment described in Example 6.

In the study, the human liver cancer cell line, HepG2 cells were treated with DMSO (vehicle control), sulforaphane (SFN), silibinin (Silib), or the combination of sulforaphane and silibinin, for 24 hours. Cell lysates were collected and glutathione levels were measured using o-phthalaldehyde (OPT) as a fluorescent reagent. FIG. 5 and FIG. 6 show the results of the study.

In Part 1 of the study, the effect of 0.5 µM SFN was compared to various concentrations of silibinin and to the combination of 0.5 µM SFN and silibinin at various concentrations. In particular, the cells were treated with one of the following: (i) DMSO (vehicle control), (ii) 0.5 µM SFN, (iii) 100 µM Silib, (iv) 200 µM Silib, (v) 300 µM Silib, (vi) 0.5 µM SFN and 100 µM Silib, (vii) 0.5 µM SFN and 200 µM Silib, and (viii) 0.5 µM SFN and 300 µM Silib. The results demonstrate that the combination of sulforaphane and silibinin at each of the tested dosages had a synergistic effect compared to each component alone. For example, when the cells were treated with individual components the glutathione levels remained the same with treatment of sulforaphane alone or decreased slightly with Silibinin treatment compared the DMSO (vehicle) control. However, when cells were treated with the combination of sulforaphane and silibinin, at each of the tested dosages, the glutathione levels synergistically increased compared to the control. An increase in glutathione levels is a beneficial effect. The results are depicted in FIG. 5.

In Part 2 of the study, the effect of 2 µM SFN was compared to various concentrations of silibinin and to the combination of 2 µM SFN and silibinin at various concentrations. In particular, the cells were treated with one of the following: (i) DMSO (vehicle control), (ii) 2 µM SFN, (iii) 100 µM Silib, (iv) 300 µM Silib, (v) 2 µM SFN and 100 µM Silib, and (vi) 0.5 µM SFN and 300 µM Silib. The results demonstrate that the combination of sulforaphane and silibinin at each of the tested dosages had a synergistic effect compared to each component alone. For example, when the cells were treated with individual components, the glutathione levels remained the same with treatment of sulforaphane alone or decreased slightly with Silibinin treatment compared to the control. However, when cells were treated with the combination of sulforaphane and silibinin, at each of the tested dosages, the glutathione levels synergistically increased compared to the control. An increase in glutathione levels is a beneficial effect to detoxify cells. The results are depicted in FIG. 6.

Example 7

A subject presents with non-alcoholic fatty liver disease (NAFLD) and is suffering from symptoms including malaise, fatigue, and abdominal discomfort. She is administered a tablet containing glucoraphanin, myrosinase, ascorbic acid, and a milk thistle extract. The tablet is an enteric coated formulation which releases the contents in the small intestine. After one month of daily administration of the tablet, the subject experiences modulation of surrogate biomarkers including glutathione which correlates with improvement in symptoms.

What is claimed:

1. An orally administrable composition comprising a synergistic combination of:
   i) a sulforaphane precursor, an enzyme capable of converting the sulforaphane precursor to sulforaphane, and an enzyme potentiator; and
   ii) a milk thistle extract or powder.

2. The orally administrable composition of claim 1, wherein the sulforaphane precursor comprises glucoraphanin.

3. The orally administrable composition of claim 1, wherein the enzyme capable of converting the sulforaphane precursor to sulforaphane comprises myrosinase.

4. The orally administrable composition of claim 1, wherein the enzyme potentiator comprises ascorbic acid.

5. The orally administrable composition of claim 1, wherein the composition comprises an enteric-coated dosage form.

6. The orally administrable composition of claim 1, further comprising one or more additional components selected from the group consisting of: quercetin, an aminosugar, a glycosaminoglycan, avocado/soybean unsaponifiables, a vitamin, coffee fruit, magnesium, proanthocyanidins, ursolic acid, curcumin, phytosterols, and phytostanols.

7. The orally administrable composition of claim 1, wherein
   i) the sulforaphane precursor comprises glucoraphanin,
   ii) the enzyme capable of converting the sulforaphane precursor to sulforaphane comprises myrosinase,
   iii) the enzyme potentiator comprises ascorbic acid, and
   iv) the milk thistle extract or powder is milk thistle extract.

8. The orally administrable composition of claim 1, wherein the sulforaphane precursor, the enzyme capable of converting the sulforaphane precursor to sulforaphane, and the enzyme potentiator are comprised in a broccoli extract or powder.

9. The orally administrable composition of claim 1, wherein
   i) the milk thistle extract or powder has silymarin, and
   ii) the orally administrable composition is formulated to provide a silymarin:sulforaphane precursor ratio of from about 1:5 to about 50:1.

10. The orally administrable composition of claim 9, wherein the silymarin:sulforaphane precursor ratio is from about 1:1 to about 4:1.

11. The orally administrable composition of claim 1, wherein
   i) the milk thistle extract or powder has silibinin, and
   ii) the orally administrable composition is formulated to provide a silibinin:sulforaphane precursor ratio of from about 1:5 to about 50:1.

12. The orally administrable composition of claim 11, wherein the silibinin:sulforaphane precursor ratio is from about 1:1 to about 13:1.

13. The orally administrable composition of claim 1, wherein the milk thistle extract or powder is standardized to include from about 5% to about 75% silibinin.

14. The orally administrable composition of claim 13, wherein the milk thistle extract or powder is standardized to include from about 20% to about 35% silibinin.

15. The orally administrable composition of claim 1, wherein the milk thistle extract or powder is standardized to include from about 25% to about 95% silymarin.

16. The orally administrable composition of claim 15, wherein the milk thistle extract or powder is standardized to include from about 55% to about 85% silymarin.

17. An orally administrable composition comprising a synergistic combination of a broccoli extract or powder and a milk thistle extract or powder, wherein
   i) the broccoli extract or powder comprises a sulforaphane precursor,
   ii) the milk thistle extract or powder has silymarin, and
   iii) the synergistic combination has a silymarin:sulforaphane precursor ratio of from about 1.5:1 to about 5:1.

18. An orally administrable composition comprising a synergistic combination of a broccoli extract or powder and a milk thistle extract or powder, wherein
   i) the broccoli extract or powder comprises a sulforaphane precursor,
   ii) the milk thistle extract or powder has silibinin, and
   iii) the synergistic combination has a silibinin:sulforaphane precursor ratio of from about 1:1 to about 20:1.

19. An orally administrable composition comprising a synergistic combination of a broccoli extract or powder and a milk thistle extract or powder, wherein
   i) the broccoli extract or powder comprises a sulforaphane,
   ii) the milk thistle extract or powder has silymarin, and
   iii) the synergistic combination has a silymarin:sulforaphane ratio of from about 5:1 to about 15:1.

20. An orally administrable composition comprising a synergistic combination of a broccoli extract or powder and a milk thistle extract or powder, wherein
   i) the broccoli extract or powder comprises a sulforaphane,
   ii) the milk thistle extract or powder has silibinin, and
   iii) the synergistic combination has a silibinin:sulforaphane ratio of from about 2:1 to about 10:1.

\* \* \* \* \*